(12) United States Patent
Zhou et al.

(10) Patent No.: US 7,011,793 B2
(45) Date of Patent: Mar. 14, 2006

(54) RECONFIGURABLE MODULAR MICROFLUIDIC SYSTEM AND METHOD OF FABRICATION

(75) Inventors: Peng Zhou, Newtown, PA (US); Lincoln Young, Ithaca, NY (US)

(73) Assignee: Kionix, Inc., Ithaca, NY (US)

( * ) Notice: Subject to any disclaimer, the term of this patent is extended or adjusted under 35 U.S.C. 154(b) by 0 days.

(21) Appl. No.: 10/807,051

(22) Filed: Mar. 23, 2004

(65) Prior Publication Data

US 2004/0228771 A1    Nov. 18, 2004

Related U.S. Application Data

(60) Provisional application No. 60/470,760, filed on May 15, 2003.

(51) Int. Cl.
*B01L 3/02* (2006.01)
*B01L 11/00* (2006.01)
*B01L 3/00* (2006.01)
*G01N 15/06* (2006.01)
*G01N 21/00* (2006.01)

(52) U.S. Cl. .......................... 422/100; 422/50; 422/55; 422/58; 422/68.1; 422/81; 422/82; 422/82.05; 422/101; 422/102; 422/103; 422/104; 436/43; 436/52; 436/53; 436/63; 29/592; 29/592.1

(58) Field of Classification Search ................. 422/50, 422/55, 58, 68.1, 81, 82, 82.05, 100, 101, 422/102, 103, 104; 436/43, 52, 53, 63; 29/592, 29/592.1
See application file for complete search history.

(56) References Cited

U.S. PATENT DOCUMENTS

| | | | |
|---|---|---|---|
| 3,548,849 A | 12/1970 | Purcell et al. | 137/81.5 |
| 3,658,088 A * | 4/1972 | Jensen et al. | 137/561 R |
| 3,993,091 A * | 11/1976 | Loveless | 137/269 |
| 4,080,752 A | 3/1978 | Burge | 46/25 |
| 4,188,977 A * | 2/1980 | Laakaniemi et al. | 137/833 |
| 5,387,395 A * | 2/1995 | Coassin et al. | 422/81 |
| 5,580,523 A | 12/1996 | Bard et al. | 422/50 |
| 5,624,638 A | 4/1997 | Negrotti | 422/61 |
| 5,640,995 A | 6/1997 | Packard et al. | 137/597 |
| 5,846,396 A | 12/1998 | Zanzucchi et al. | 204/601 |
| 5,955,028 A | 9/1999 | Chow | 422/63 |
| 5,989,402 A * | 11/1999 | Chow et al. | 204/601 |
| 6,033,544 A | 3/2000 | Demers et al. | 204/450 |
| 6,071,478 A * | 6/2000 | Chow | 422/81 |
| 6,086,740 A | 7/2000 | Kennedy | 204/601 |

(Continued)

FOREIGN PATENT DOCUMENTS

| | | |
|---|---|---|
| EP | 1203954 | 5/2002 |
| WO | WO01/70400 | 9/2001 |
| WO | WO02/30560 | 4/2002 |

OTHER PUBLICATIONS

Paul Yager, PhD—Dept. Bioengineering, U. Washington A part of "Microfluidics—A Highly Biased Primer" (2001).

(Continued)

*Primary Examiner*—Brian J. Sines
(74) *Attorney, Agent, or Firm*—Brown & Michaels, PC

(57) ABSTRACT

A reconfigurable modular microfluidic system, providing a microfluidic breadboard platform for the formation of fluidic network and fluidic sealing upon a system assembly. Modular microfluidic elements or "chips" are arranged on a precisely machined alignment base to form a fluidic network, with fluid connections provided directly from chip-to-chip at overlapping corners. Fluidic access to external devices is possible at every fluid connection and through special ingress/egress chips. By maintaining a largely planar layout, optical access is provided for detecting or visualization for every chip. The assembly may be covered by a perforated cover plate.

31 Claims, 7 Drawing Sheets

U.S. PATENT DOCUMENTS

| | | | |
|---|---|---|---|
| 6,090,251 A * | 7/2000 | Sundberg et al. | 204/453 |
| 6,132,685 A * | 10/2000 | Kercso et al. | 422/104 |
| 6,167,910 B1 * | 1/2001 | Chow | 137/827 |
| 6,284,113 B1 | 9/2001 | Bjornson et al. | 204/453 |
| 6,290,791 B1 * | 9/2001 | Shaw et al. | 156/64 |
| 6,358,387 B1 | 3/2002 | Kopf-Sill et al. | 204/603 |
| 6,827,831 B1 * | 12/2004 | Chow et al. | 204/604 |
| 6,845,787 B1 * | 1/2005 | Karp et al. | 137/833 |
| 2002/0028504 A1 | 3/2002 | MacCaskill et al. | 435/289.1 |
| 2002/0124896 A1 | 9/2002 | O'Connor et al. | 137/833 |
| 2002/0143437 A1 | 10/2002 | Handique et al. | 700/266 |
| 2002/0187074 A1 | 12/2002 | O'Connor et al. | 422/82.5 |
| 2002/0192112 A1 | 12/2002 | Chow | 422/63 |
| 2003/0012697 A1 | 1/2003 | Hahn et al. | 422/99 |
| 2003/0021725 A1 | 1/2003 | Unno et al. | 422/50 |

OTHER PUBLICATIONS

LioniX Modular Lab/Process on a Chip http://www.lionix-bv.nl/pdf/news_flyers_microfluidics.pdf.

Packaging Technology for Miniature IVD Instrumentation. Gonzalez, Pan, Collins & Smith—*Medical Device & Diagnostic Industry* (Apr. 1998) http://www.devicelink.com/mddi/archive/98/04/010.html.

A World-to-Chip Socket for Microfluidic Prototype Development Yang Z and Maeda R (2002) *Electrophoresis* 23 (20) 3474-3478.

The Optimal Configuration of Mechatronic Products with Integrated Microsystem Technology Components. Zöppig, et al Limenau Technical University, Drive Engineering Group (2000).

CAT Expands MEMS Packaging Cababilities. Center for Automation Technologies at RPI—Web page (2002) http://www.cat.rpi.edu/MEMS_packaging.htm.

A New Microfluidic Paradigm for Biological and Biochemical Research. http://faculty.washington.edu/yagerp/microfluidicstutorial/newparadigm/newparadigm.htm.

* cited by examiner

RECONFIGURABLE MODULAR MICROFLUIDIC SYSTEM AND METHOD OF FABRICATION

REFERENCE TO RELATED APPLICATIONS

This application claims an invention which was disclosed in Provisional Application No. 60/470,760, filed May 15, 2003, entitled "RECONFIGURABLE MODULAR MICROFLUIDIC SYSTEM AND METHOD OF FABRICATION". The benefit under 35 USC § 119(e) of the United States provisional application is hereby claimed, and the aforementioned application is hereby incorporated herein by reference.

BACKGROUND OF THE INVENTION

1. Field of the Invention

The invention pertains to the field of miniaturized chemical and biochemical fluid management systems using microfluidic technology. In particular, the invention relates to the design and fabrication of reconfigurable microfluidic systems using discrete devices and other building blocks on a "breadboard" base.

2. Description of Related Art

The concept of the breadboard is well known to those familiar with electronics and electronic circuits. The term "breadboard" derives from the earliest days of electrical experimentation, when circuits were literally built on a base made from a wooden breadboard.

In the electronics lab, the breadboard system allows an investigator to quickly build a test version of a potentially useful circuit from discrete electronic components. The breadboard framework allows the experimenter to construct a circuit with minimum effort, subsequently enabling the testing of certain values at important locations in the circuit.

For an electronic circuit, voltage, current and resistance are important factors to be tested. The components are standardized—IC chips, resistors, capacitors, etc., often with a standardized spacing of connections. Once the circuit has been sufficiently tested, a copy can be made in a printed circuit board, or as a mass produced integrated circuit. The breadboard enables one to design and test novel circuits, and sub-circuits, while mitigating the prohibitively expensive process of producing multiple revisions in a mass production environment.

The breadboard concept is useful in developing integrated microfluidic systems as well. Instead of voltage, current and resistance, the variables governing microfluidic experiments are typically flow rate, pressure, and concentration, but the utility of easily reconfigured systems by the user is the same.

One of the most attractive features for developing microfluidic systems for life science research is the potential integration of a series of sequential operations on a single device. However, there are inherent difficulties for developing high efficiency, fully integrated microfluidic applications. First, to establish some baseline parameters for the design of an optimized device, sequential operations are preferably developed and characterized in a discrete manner before system integration. This discretization allows the developer to reduce a complex, multi-variable challenge into many smaller, manageable problems and tackle them individually. On the other hand, it is often impossible to test each section of a system in isolation before attempting integration; many components do not provide meaningful information until they are assimilated into the system as a whole. The demand to isolate the specific impact of an individual module in a sequential operation in addition to the ability to investigate the overall performance for the integrated device present an unmet challenge for microfluidic developers.

A framework for the compilation of modular microfluidic chips, i.e. a "microfluidic breadboard", would allow the developers to test, alter and retest components in a synchronous fluid management environment which mimics the integrated device without the cost and delay of multiple complete system revisions. However, unlike electronics, there is no standardization of discrete microfluidic components which lend themselves to easy breadboarding, as do the standardized components and packaging of electronic components. Also, the routing of fluids encounters difficulties that are not presented when conducting electrons through wires in electronic circuits.

In an electronic breadboard, each of the components is supplied with leads that allow it to be wired into the system as a whole. In a fluid management system, tubes or channels must be provided to route the fluid through the system. Fluid leakage, chemical stability of the sealing materials, contamination and cross talk, capillary forces, and void volume must all be considered when designing microfluidic systems. This requires seals made from a material that is chemically compatible with the fluid retained by the system to provide adequate sealing at the required pressure. The seal and design of fluid passage between adjoining devices must prevent the fluid from escaping the intended route; it must do so with a minimum of swept volume in order to maximize the performance of the overall system.

Currently, the limited options to join discrete microfluidic components to form fluidic network are almost exclusively based on using epoxy with standard capillaries or "Nanoport" fittings made by Upchurch Scientific, a division of Scivex, Oak Harbor, Wash. While the former method is straightforward and widely utilized by many researchers, its cumbersome nature during the capillary and system assembly makes the process very tedious and time consuming. The length of capillary required to make connections increases the overall system length, resulting in higher flow resistances and difficulty when balancing the flow in parallel branches of a system. The complexity of such a capillary network scales up rapidly such that even in the integration of a modest number of microfluidic components, the "plumbing" would become excessively complex. Additionally, the components used in an assembled system are not readily reusable. NanoPort fittings do not suffer from all of the drawbacks of epoxy, but they require precision alignment to the fluid communication port of the microfluidic chip; aligning two 100 μm scale holes via a compressible ferrule is not at all trivial.

It is also important that optical access into the components of a system be maintained—that is, the individual devices or "chips" must not be obscured from view by the breadboard base or other fittings. Although the fittings that Upchurch Scientific provides are relatively small, in comparison to the chip scale devices to which they attach, they require a bonding area that can exceed the active device area of the fluidic chip. For this reason, there can be difficulties with obscuring the optical access to the active area of the chip. A method is required that allows devices to be easily placed and repositioned while minimizing interval volume as well as assuring optical and fluidic access.

Purcell's U.S. Pat. No. 3,548,849, "Fluidic Circuit Package", discloses means of stacking fluidic components that provides for the synthesis of a microfluidic circuit. However, the stacking of chips, while making the sealing of the components simpler, eliminates the investigator's ability to monitor the system optically. The stacked scheme also restricts fluid delivery by limiting the available locations for ingress or egress. The purpose of Purcell's work was to provide a means for producing fluidic circuits in order to replace electronic circuits, not to allow for chemical and biochemical reaction and analysis.

Bard's U.S. Pat. No. 5,580,523, "Integrated Chemical Synthesizers" and Hahn's Published Application No. 2003/0012697 "Assembly Microchip Using Microfluidic Breadboard" disclose means for producing detachable microfluidic systems. In both of these cases, a "motherboard" structure is required to complete the transport of the fluid through the system. This "motherboard" comprises a series of channels in a substrate to which the chips are subsequently connected at predetermined locations. This scheme necessitates adherence to a set base pattern; the flexibility of the system is restricted by the "motherboard" design. The base pattern is predefined and limits the overall microfluidic network configurability.

Kennedy's U.S. Pat. No. 6,086,740, "Multiplexed microfluidic devices and systems" and O'Connor's published application No. 2002/0124896, "Modular microfluidic systems" outline two systems which are created for specific experiments. As in Bard, fluids in these systems are routed from devices through channels in the motherboards.

SUMMARY OF THE INVENTION

The system outlined in this invention uses direct interconnection between modular microfluidic devices ("chips" or "modules") to form a fluidic network, therefore, there is no rigid predefined fluidic pathways. Fluidic access to external devices is possible at every fluid connection. By maintaining a largely planar layout, optical access is provided for detecting or visualization of every chip. The microfluidic breadboard of the invention is not designed to complete a single, specific, predetermined task—rather, the present invention is designed for reconfigurability to allow testing of a variety of potential microfluidic system designs.

The microfluidic breadboard described in this invention differentiates itself from the prior art by providing a microfluidic breadboard platform for the formation of fluidic networks and fluidic sealing upon system assembly. In a preferred embodiment the breadboard comprises an array of perforated pockets or wells to hold modules/chips on a precisely machined alignment base. The assembly may be covered by a perforated cover plate. The wells and the modules preferably have a consistent shape.

The chips may be constructed from a lamination of substrates comprising functional microfluidic features. These features can be accessed through a fluidic communication port or ports on the chip surface, surrounded by a sealing feature. The chips are constructed, and the alignment base is arranged, to provide for overlapping fluid conducting ports in the corners of each chip. Holes in the alignment base then provide a means of egress or ingress of a fluid via connectors and/or provide pressure for sealing at each corner port of every chip location. The chips are designed in three groups: devices that perform specific functions; logic components, and ingress-egress chips that provide means of conducting fluids to desired locations. A complete fluid management system can be constructed by placing the chips into the alignment base in such a way as is desired to carry out the required tasks.

The base or breadboard is designed and constructed to ensure that when chips are placed into the base plate locating pockets, the fluidic communication ports at each corner of the chip are overlapped to generate a unique application specific fluid network. The leak-free chip-to-chip sealing with minimum void volume is achieved by mating the chip loaded base plate with a perforated cover plate and applying adequate pressure at each corner of the microfluidic chip by using either NanoPort fittings or pre-loaded screws.

In contrast to the prior art, then, the logic and functional chips of the present invention determine the path of the fluid. They can be juxtaposed to fit any layout required. This gives the present system a level of reconfigurability not provided by a "motherboard" based technology.

According to this invention, the combination of prefabricated pockets for chip alignment, overlapped corner fluid communication port, on-chip sealing means and the flexibility of egress or ingress of a fluid at any fluid communication port provides true chip-level reconfigurability and reusability that is not realized in existing technologies. Upon the completion of or during an investigation, any of the components of the fluid network can be released, replaced or repositioned without disturbing the surrounding components in the system. This arrangement therefore provides the maximum configuration efficiency by keeping the complete assembled fluid network undisrupted during the replacement of the chips and complete network flexibility in that each component of the fluid system can be independently replaced and tested.

A further embodiment of this invention is that the system provides optical access for fluid visualization or molecular detection on each chip. For any microfluidic application development work, optical access to the fluidic channels is of paramount importance for microscopic or unaided visual inspection, ultraviolet detection or other means. To provide the maximum optical accessibility, the present invention incorporates a perforated cover and base plates to hold microfluidic chips. Each chip preferably includes an optically transparent cover lid. When the chip is positioned in the base plate, the optically transparent side is aligned atop or beneath a viewing window to allow free optical access. This configuration greatly enhances the usability of the breadboard system described herein.

In order to establish unrestricted fluid ingress or egress at arbitrary fluid communication ports upon system assembly, the present invention provides a means for chip-based fluid connection. In one preferred embodiment, the fluid connection chip is constructed by a particular connecting pattern between the fluid communication ports situated at each corner of the chip to a group of capillaries located in the center. For a chip with four corner fluid communication ports, there are five unique patterns to cover all possible fluid delivery combinations. The five fluid communication chips thus provide a novel modular and reusable fluid ingress or egress method.

BRIEF DESCRIPTION OF THE DRAWINGS

FIG. 2b shows a chip cross-section along the line 2b—2b in FIG. 2a.

DETAILED DESCRIPTION OF THE INVENTION

The present invention addresses the need for rapidly building an application specific microfluidic chemical analysis system from standardized components.

The system of the invention is constructed from a multiplicity of discrete modular microfluidic devices or "chips", assembled on an alignment base ("breadboard"). The chips are standardized as to shape, size and thickness, allowing great flexibility in assembly of the chips as needed.

Module/Chip Structure

In one embodiment of the invention, the chips (microfluidic modules) are essentially square in layout, with a fluid passage or hole (fluid communication port) located at each corner of the chip, surrounded by a sealing feature. The square layout of the chip allows the chips to be arranged in a diagonal array, meaning only one corner of adjacent chips overlap. The diagonal array permitted by this arrangement of square chips and four corner holes gives the ability to branch the fluid path without making special provision in the alignment base. A square chip gives the ability to align the chip in four distinct rotational positions, which is not the case with irregular polygons. Having four positions allows a design which dramatically lessens the number of logic chips needed to maintain flexibility. In other embodiments, the fluid passages are located, alternatively or in addition to locations in the corners, in the center and/or the sides of the microfluidic modules.

Some other regular polygonal shape could be substituted for the square, including, but not limited to, a triangle, a rectangle, or a hexagon, but with drawbacks. A hexagon can be complicated as far as logic is concerned, and would give rise to problems in manufacture. If a rectangle were used, only two positions would be possible to fit into a prefabricated pocket. Circular chips could be employed, but would be less space efficient and would present alignment difficulties. The same considerations apply for using only four holes. If eight were used, for example, the logic would be more difficult to manage. These factors argue in favor of square chips with four corner ports to allow the building of highly complex systems with a very limited number of chip variations.

All of the chips are positioned relative to each other in an alignment base. The alignment base assures that the fluid communication ports on each of the chips align with those of the adjacent chips, so that fluid can flow directly between the chips without leakage and without unnecessary interconnecting tubing, voids or volumes. The alignment base and chips are then preferably secured via a cover.

Figure 1:
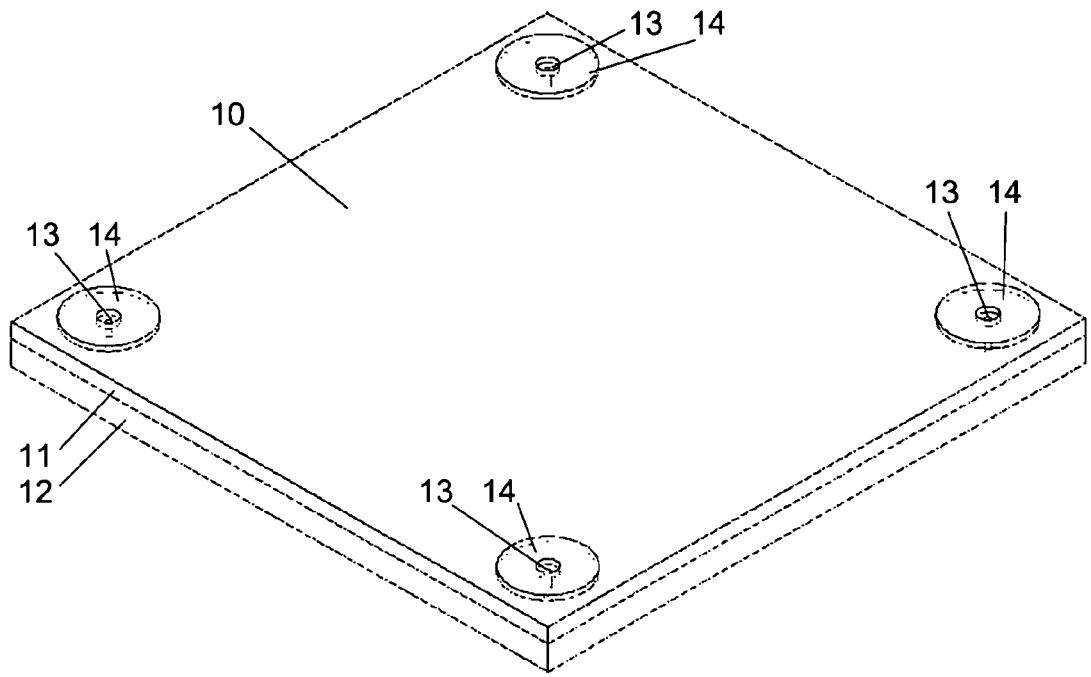
FIG. 1 shows an isometric view of chip layout.

FIG. 1 shows an isometric view of a fluidic chip 10 which can be used with the invention. The chip is constructed from two or more layers 11, 12. These layers can be made of a variety of materials such as silicon, glass or plastic. Layer 12 is patterned with the chosen fluid passageways or specific features ("microfluidic architecture"). Ports 13 are provided normal to the substrate surface connecting to the microfluidic architecture. Sealing means 14 are provided to seal between chips and to external connectors.

The seals 14 can be made from any of a group of polymers exhibiting the required elasticity and chemical resistance, for example, silicone, fluoropolymer, fluorosilicone, latex, or polyamide. The material may be patterned by photolithography, screen-printing, lamination, cut sheet, injection molding or direct deposition, these being suitable processes for wafer level parallel processing.

Figure 2A:
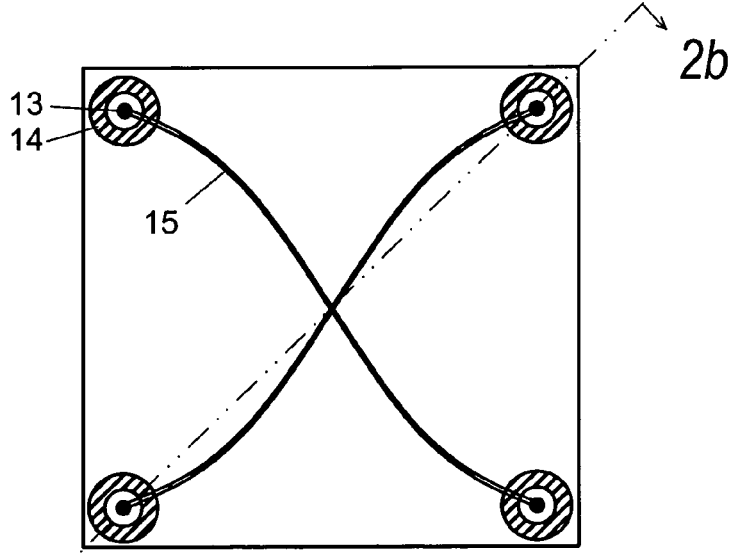
FIG. 2a shows a chip top view.
Figure 2B:
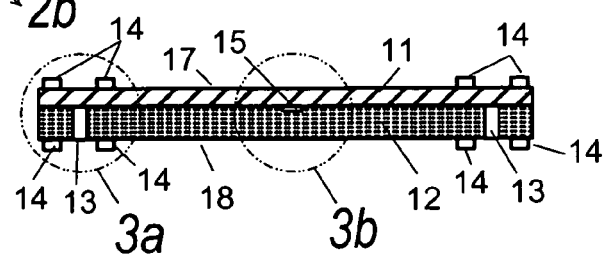
Figure 3A:
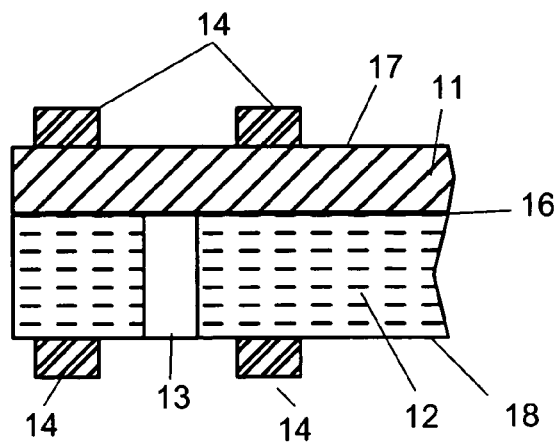
FIGS. 3a and 3b show chip cross section details as indicated by circles 3a and 3b in FIG. 2b.
Figure 3B:
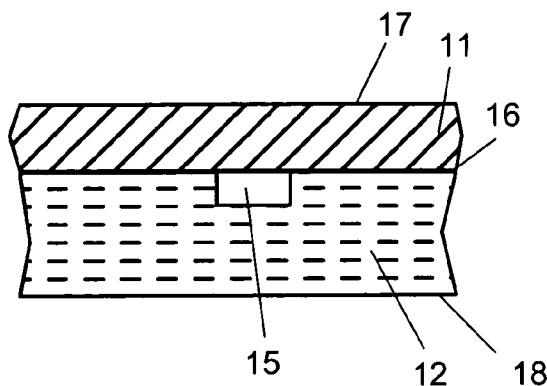
Figure 4:
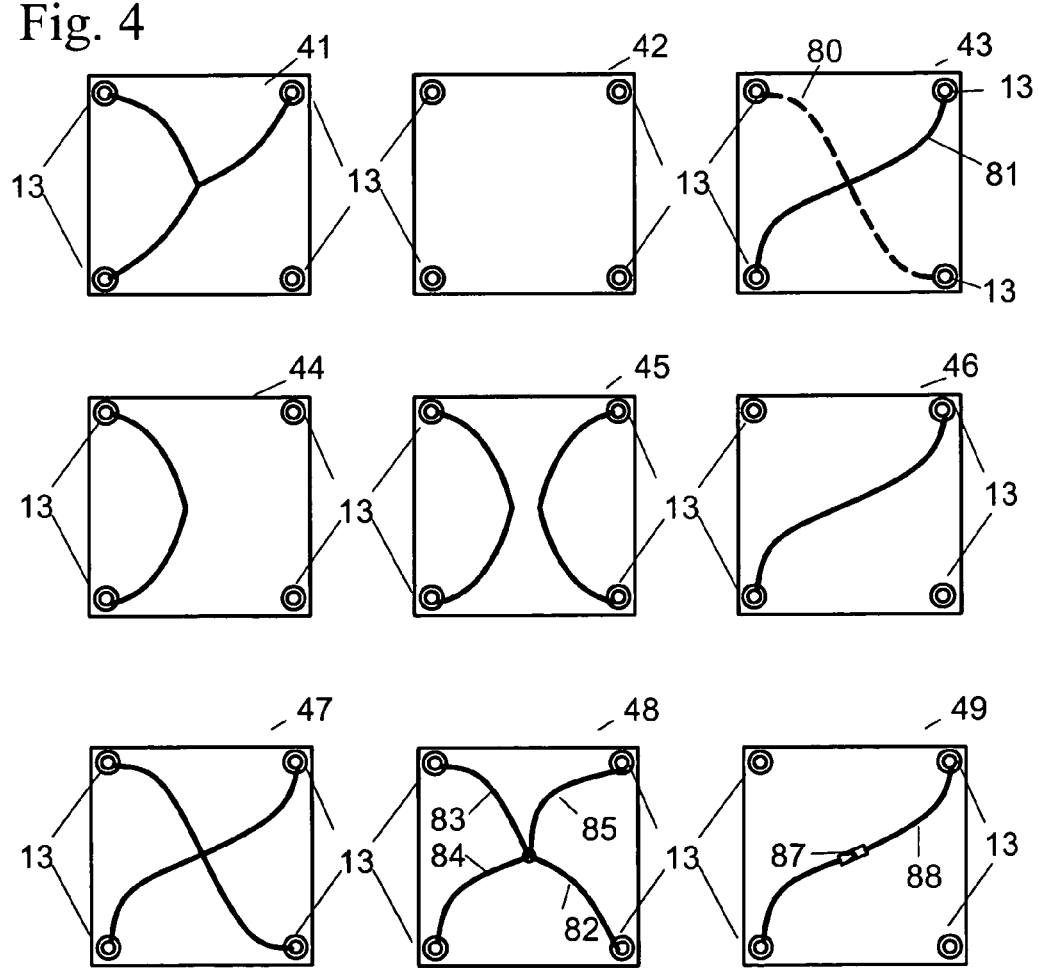
FIG. 4 shows sample logic chips.

FIG. 2a shows the top of a fluidic chip 10, in this case a logic chip of the "cross" type shown at 47 in FIG. 4. FIG. 2b shows a cross section of the chip, along line 2b—2b in FIG. 2a. FIG. 3 shows details of the cross sectional view of the chip, as indicated by circles 3a and 3b in FIG. 2b.

The microfluidic channel 15 of the logic chip can be seen patterned in the surface of substrate 12. This pattern may be created by means of etching in silicon, specifically Deep Reactive Ion Etching (DRIE), by machining or by wet chemical etching. Similar means may be useful for patterning glass substrates. In the case of plastics, injection molding, embossing, casting, or machining may be suitable.

The ports 13 may be created by DRIE, laser, or ultrasonic machining in silicon; laser, wet chemical etching or ultrasonic machining in glass; and laser or standard machining, or as part of the injection molding process in plastic. Any of the two or more substrates, 11 and 12, may have ports 13 provided allowing fluid to pass from either side of the chip to architecture 15 at the interface 16; or to pass completely through the chip; or a port or ports can be left out to provide a stoppage. In the example shown, the port 13 is only in substrate 12, and is blocked off at substrate 11.

The two substrates, 11 and 12, are then sealed together to form an enclosed microfluidic structure. This interface 16 can be sealed by any suitable means—anodic or fusion bonding for glass/silicon, silicon/silicon and glass/glass substrates; adhesive bonds for glass, plastic, or silicon combinations; and direct lamination for plastic substrate stacks.

The chip sealing pads 14 are provided on both surfaces 17 and 18 of the chip. The seals provide sealing between chips when placed face to face, or seal against the cover or the alignment base, to be discussed below.

Types of Chips

The chips are grouped into three categories: those that serve to direct the fluid flow are called "logic chips", those which provide inlets and outlets are called "ingress/egress chips" and those that perform a specific chemical or biological or other function are called "functional chips".

FIG. 4 shows various types of logic chips, which can be used with the invention. The purpose of the logic chips, as mentioned above, is to route the fluid to the desired locations through a specific layout. Each of the chips has at least one corner port 13, although in some variations the ports are not connected to any channels within the chip. In FIG. 4, the chips each have four corner ports 13. Eight combinations of connections between the ports in FIG. 4 are shown. Each of the logic chips is preferably designed to be an equal path length from port to port to assure pressure balanced, predictable flow.

Chip 41 is the equivalent of a "T" connection. Preferably, as shown, the channels are structured to maintain no preferential flow by intersecting at 120-degree angles.

Chip 42 is simply a blank chip that could provide a "plug" or be used as a spacer in the system. The corner ports 13 could be through holes, or plugged, as desired.

Chip 43 is a "cross over", allowing fluid to pass diagonally between opposite corners in two separate paths 80 and 81 without intermixing. This chip would require a three-layer construction. The middle layer would contain a channel defined on each of its faces, with the appropriate corners ported through the lid or both the lid and middle substrate respectively, to form the two fluid paths.

Chip 44 is an inline connection, as is chip 45 with the exception that 45 contains two channels in parallel. By rotating chip 44 into each of its four possible orientations, paths between adjoining chips can be established. Similarly, chip 45 can be rotated into two positions, so that adjoining chips horizontally or vertically can be connected.

Chip 46 is an inline connection from corner to corner, this being the single channel version of chip 43.

Chip 47 is a commonly referred to as a "cross"—the arrangement of channels is the same as in chip 43, but on only one layer, so that all of the ports 13 are connected together.

The logic chips described above are all passive conduits, but it is possible within the teachings of the invention to have logic chips which allow control of fluid flow. As examples, chip 48 is a fluidic switch, in which flow from channel 82 may be switched to channels 83 or 84 by pressure in channel 85 (or, in the inverse, flow from channels 83 or 84 might be selected to flow into channel 82) and chip 49 shows a logic chip which has a one-way ("check") valve 87 in channel 86.

Other active and passive logic chip designs are possible within the teachings of the invention.

Figure 5:
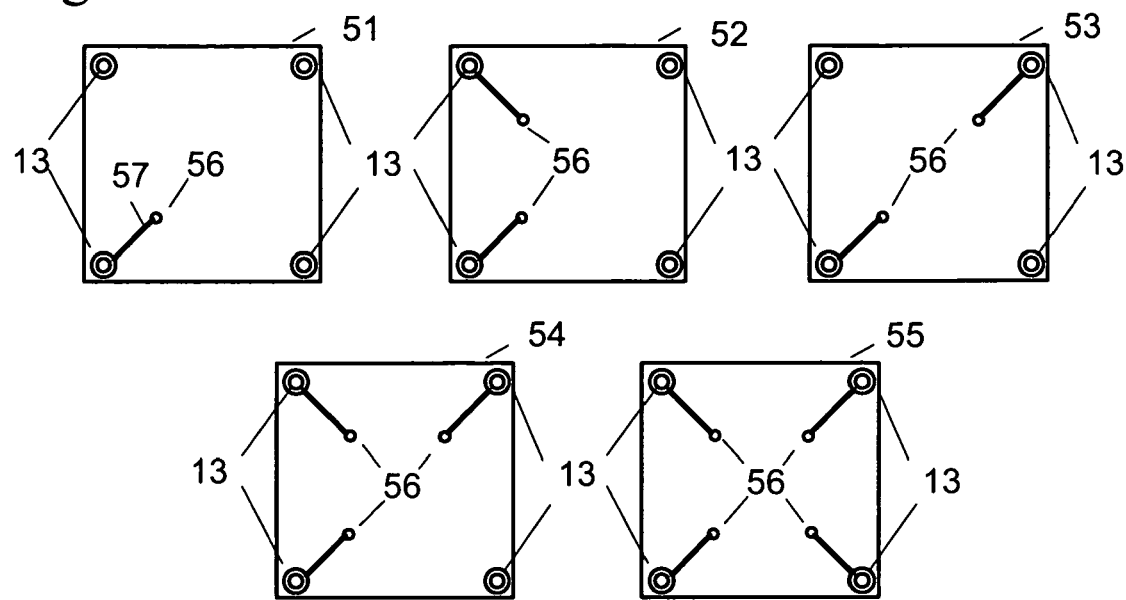
FIG. 5 shows sample fluid ingress/egress chips.

FIG. 5 shows various examples of fluid ingress/egress chips. Each of the fluid ingress/egress chips provide access to the ports 13 directly from a capillary tube 56. The capillary tube 56 is preferably a fused silica drawn tube with a polyamide coating. Its outside dimensions are preferably between 50 and 700 μm. This tube would be inserted and fixed into a hole located through the lid of the chip. This hole would provide fluid passage from the capillary to the channel 57 as well as alignment and anchorage for the capillary 56.

The various chips shown in FIG. 5 are the preferred embodiments. Each of these variations allow for connections to any or all of the fluid access points in the fluid layout. For example, chip 51 could connect to any individual corner port (simple by rotating in quarter turn increments), while chip 55 would connect to all of the corners. Chips 52 and 53 have two connections, vertical/horizontal or diagonal, respectively, and chip 54 has three connections with the fourth blanked off. It will be understood that other ingress/egress chip designs would be possible within the teachings of the invention, and that the ingress/egress design could be combined with one of the logic chip designs if desired.

Figure 6:
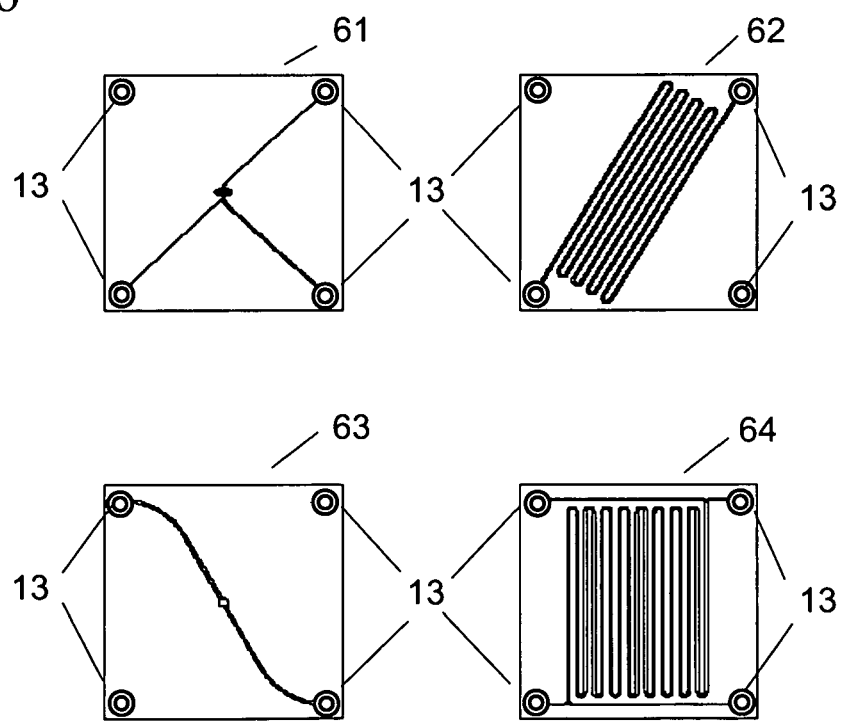
FIG. 6 shows sample functional chips.

FIG. 6 shows several possible functional chips which could be used with the invention. These sample chips are a mixer 61, a liquid chromatography column 62, a flow cell for use with a UV spectrometer 63, and a liquid extraction column 64. Other functional chips could be used within the teachings of the invention, such as micropumps, heaters, electrospray or electrophoresis apparatus, reservoirs or reactors, or sensors of various kinds such as pressure, flow, conductivity, temperature or density.

The Alignment Base and Cover Assemblies

Figure 7:
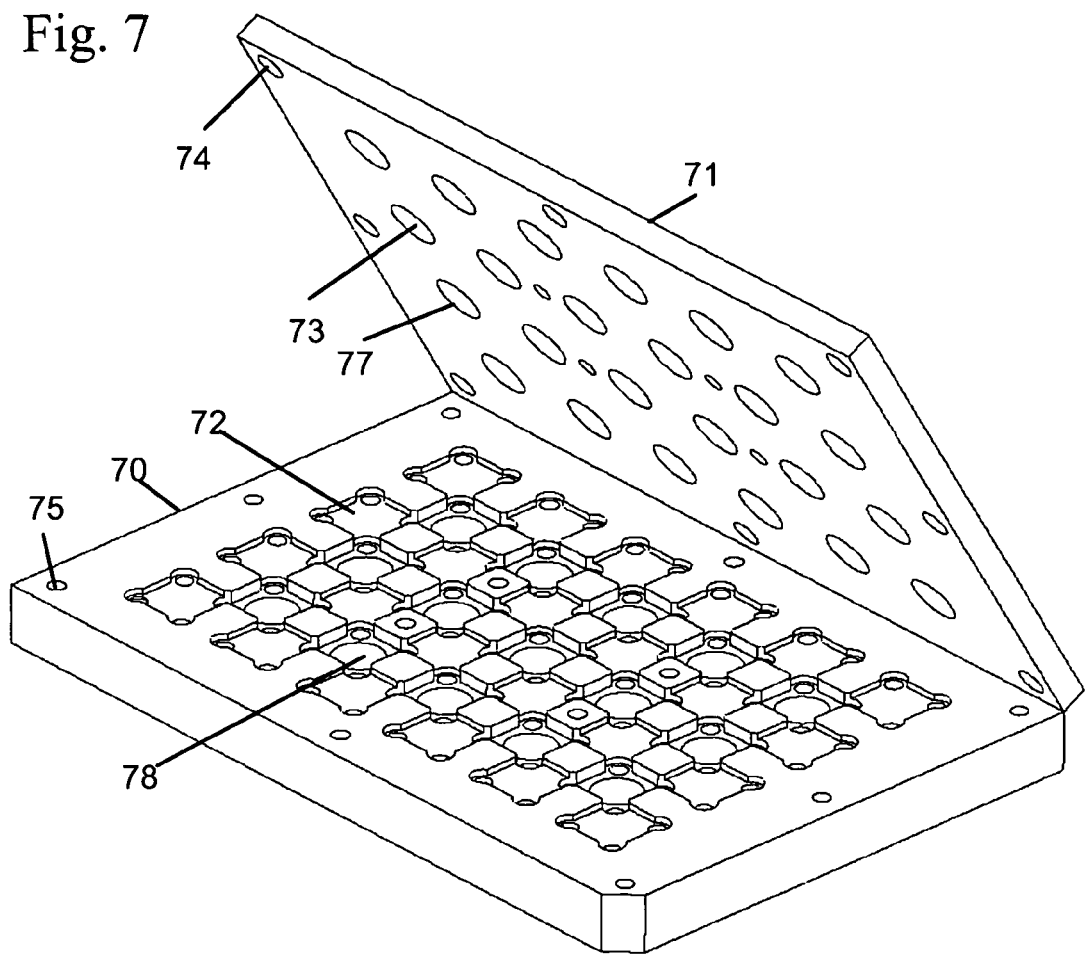
FIG. 7 shows an isometric view of the breadboard system, with base and cover.
Figure 8:
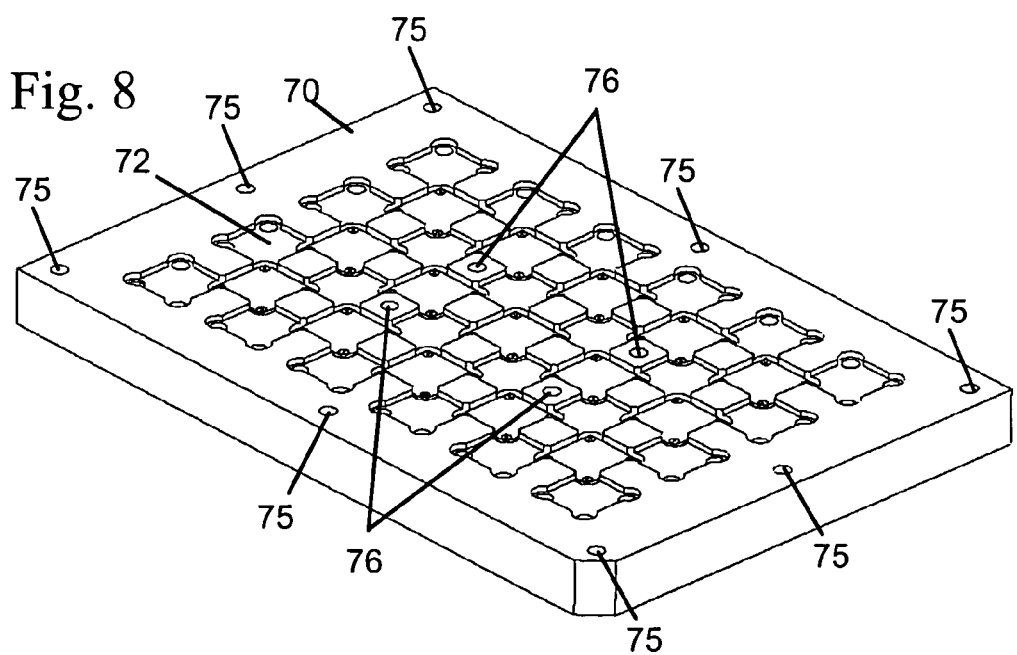
FIG. 8 shows an isometric view of an alignment base.
Figure 9:
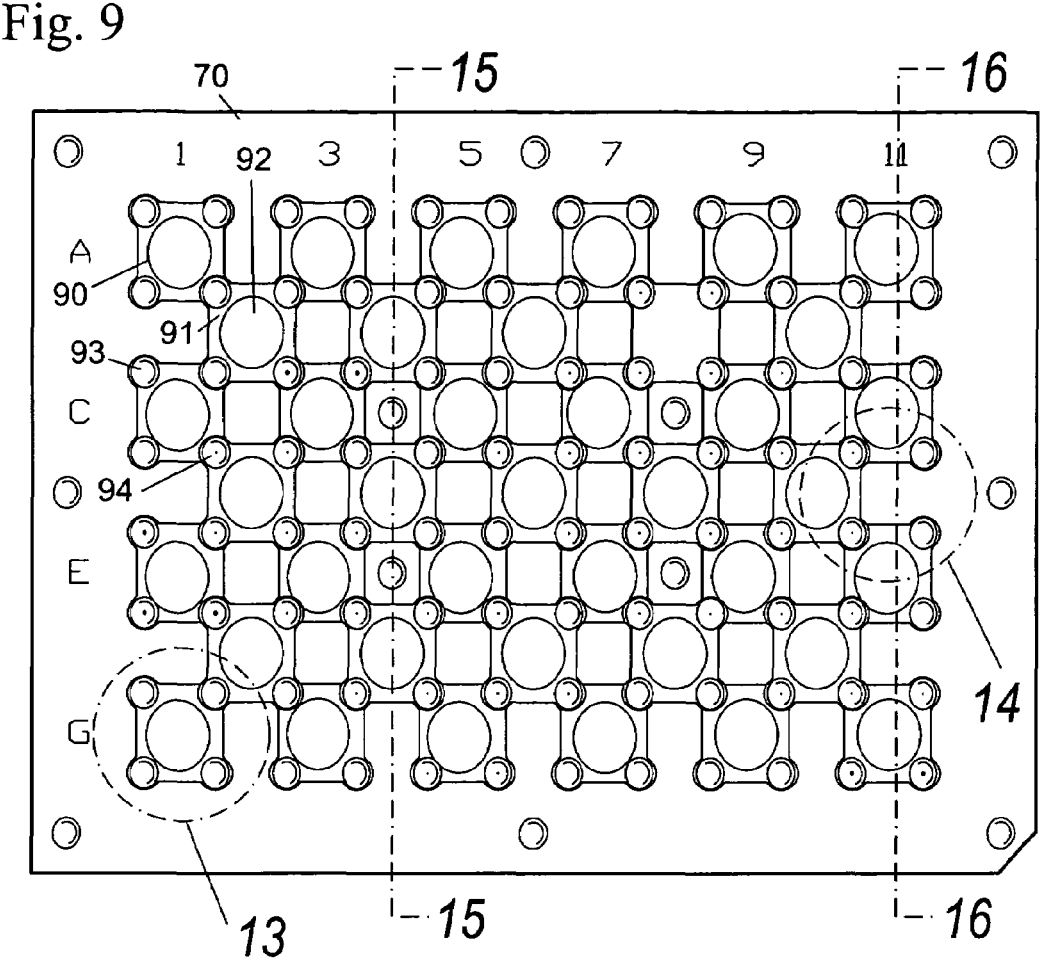
FIG. 9 shows a top view of the alignment base.
Figure 13:
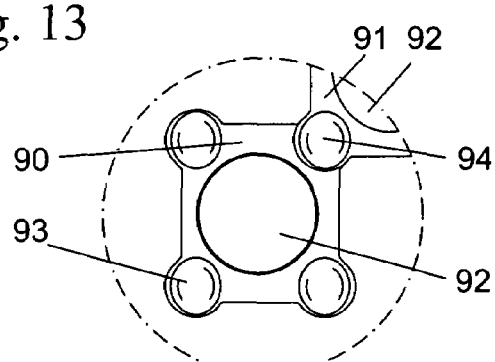
FIG. 13 shows a detail of the alignment base, in circle 13 in FIG. 9.
Figure 14:
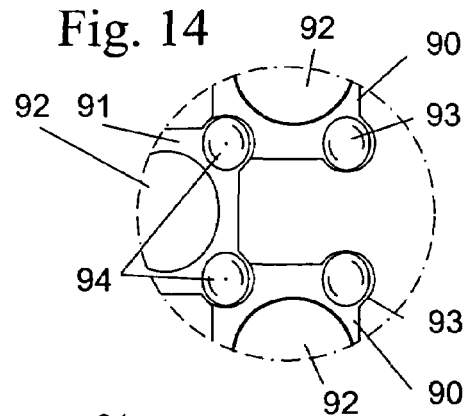
FIG. 14 shows a detail of the alignment base, in circle 14 in FIG. 9.
Figure 15:
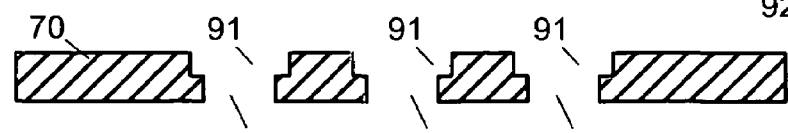
FIG. 15 shows a section view of the alignment base, along line 15—15 in FIG. 9.
Figure 16:
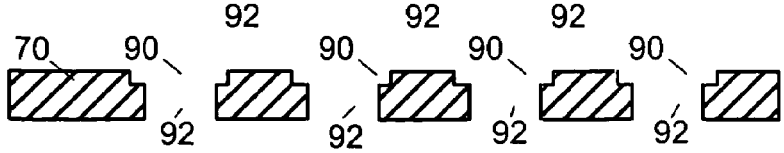
FIG. 16 shows a section view of the alignment base, along line 16—16 in FIG. 9.

FIGS. 7 and 8 show isometric views of the alignment base 70 for use with the system of the invention. In FIG. 7, the cover plate 71 is shown hinged to the base. FIG. 9 shows a top view of the alignment base, with details shown in FIGS. 13 and 14, and cross section views in FIGS. 15 and 16.

Referring to FIGS. 7 and 8, the alignment base has an orthogonal arrangement of rows and columns of wells 72 into which the chips are placed. As can be seen in FIG. 9, the rows and columns of wells can be designated by letters or numbers for ease of reference. In this explanation, the locations on the base will be denoted by letters for rows and numbers for columns, such that location E1 is the fifth row from the top, first column from the left.

While the figures show the wells in eleven columns and seven rows in a rectangular base, it will be recognized that other arrangements are possible, depending on the base shape desired. For example, both the base and the wells could be in a square shape, or the base could be round with the rows and columns of wells arranged to fill. A linear arrangement is possible as well as, for example, three rows and ten or more columns.

In FIGS. 7 and 8, optical access holes are shown at 78 in the base and 73 and 77 in the cover—it will be noted that FIGS. 7 and 8 show these holes in the odd-numbered columns in the base and the even-numbered columns in the cover, but in a preferred embodiment all of the wells are provided with optical access holes, both in the base and the cover. Although not shown, in one embodiment, the cover plate provides fluid access holes to the fluid communication ports in the microfluidic modules.

Holes 75 and 76 in the base and 74 in the cover allow base and cover to be tightened together by screws, if desired.

Referring to FIGS. 9 and 13–16, it can be seen that the wells are of two kinds, deep and shallow. The deep wells 91 are in the five even-numbered columns, the shallow wells 90 in the six odd-numbered columns. The wells are positioned so that the corners of the wells in adjacent columns overlap, allowing chips to overlap on their corners 94. The chips in the deep wells 91 are thus positioned so that their corner ports 13 (FIGS. 1–3) are precisely aligned underneath the corner ports 13 of the chips in the shallow wells 90.

Each corner of each well 90 and 91 is preferably provided with a threaded through-hole 93, which extends from the well completely through the base 70. This allows insertion of fluidic connectors or screws from underneath the base 70, as will be seen in the discussion of FIG. 11, below.

In the figure shown, the wells 90 and 91 have optical windows or holes for optical or other access from underneath the chips.

Figure 12:
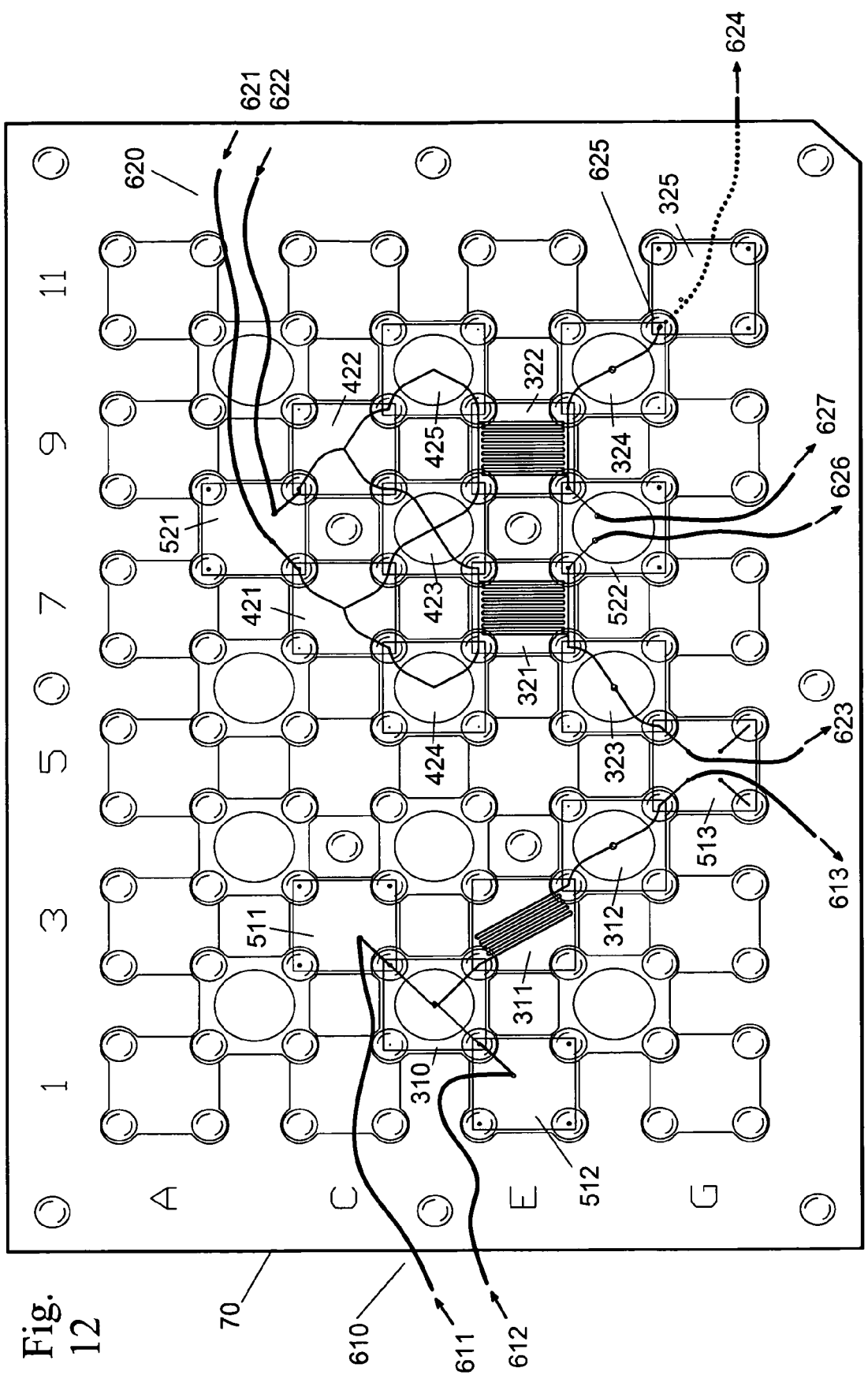
FIG. 12 shows a top view of the system of the invention with chips on the alignment base.

FIG. 12 shows a base plate 70 in which two complete microfluidic "circuits" 610 and 620 are assembled.

For ease of reference in this figure, functional chips have been assigned "300" series reference numbers, logic chips are in the "400" series, and ingress/egress chips have "500" numbers. Fluid circuits or flows are "600" series numbers. The second digit of the reference number is the fluidic circuit number, so that chip 310 would be a functional chip in the first microfluidic circuit, chip 522 an ingress/egress chip in the second circuit.

The first system is a liquid chromatography separation arrangement. It consists of three functional chips, three logic chips and three ingress/egress chips.

The setup begins in wells E1 and C3 with two fluid ingress lines 611 and 612, leading to chips 511 and 512, both single-capillary ingress/egress chips of the type shown at 51 in FIG. 5.

A mixer 310 is located in deep well D2, which puts two of its corner ports underneath the corner ports of ingress/ egress chips 511 and 512. The mixer 310 mixes flows 611 and 612, and the output of the mixer 310 goes to the corner port which overlaps the corner port of liquid chromatography column chip 311 in well E3. In turn, the output port of chip 311 overlaps the input of UV detection flow cell chip 312.

Finally, the flow 613 exits from one of the capillaries of fluid egress chip 513. As can be seen, chip 513 is a four-capillary chip as shown at 55 in FIG. 5, but only two of the ports are used—one for this circuit, one for outflow 623 of circuit 620. This illustrates the flexibility of the system, as one chip can be used for more than one circuit, and the unused ports merely communicate with corners of the well without introducing any unwanted voids or leakages into the circuits.

The second circuit 620 is a parallel liquid/liquid extraction configuration.

Two immiscible fluids 621 and 622 are introduced into the two capillaries of ingress/egress chip 521 in well B8. This chip overlaps with logic chips 421 and 422 in wells C7 and C9, respectively, which are divider chips of the sort shown at 41 in FIG. 4. The chips 421 and 422 divide the fluids 621 and 622, and half of each is supplied to an input of non-contact cross over logic chip 423 in D8, which is the kind shown at 43 in FIG. 4. The other half of each flow is routed from chips 421 and 422 to inline connection chips 424 and 425, respectively. Chips 424 and 425 are of the kind shown at 44 in FIG. 4. As can be seen, the chips have been rotated 180° with respect to each other, allowing the same type of chip to be used in both locations, routing fluid through different sets of ports.

The four flows then proceed into two liquid extraction chips 321 in well E7 and 322 in E9. Chip 321 is fed from chip 424 by half of flow 621, and from one of the paths in chip 423 by half of flow 622. Similarly, chip 322 is fed from chip 425 by half of flow 622, and from the other path in chip 423 by half of flow 621.

The output flow from chip 321 is routed into flow cell 323, and then exits as flow 623 through one capillary of ingress/egress chip 513. The output flow from chip 322 is routed into flow cell 324, and is collected through a Nanoport fitting 625 threaded through the bottom of the base 70, to exit as flow 624. A blanked or spacer chip 325, of the kind shown at 42 in FIG. 4, provides the proper spacing and prevents leakage The two remaining flows are collected through an egress chip 522 without detection, and exit as flows 626 and 627.

From above description, it becomes apparent to those skilled in the field to realize that many different configurations with a wide range of devices on the breadboard can be achieved.

For example, micromachined pumps, valves and different types of sensors can be placed at the appropriate location to deliver fluid, control the flow direction and detecting molecular or electronic signals. A UV flow cell 330 can be replaced or followed by a chip with shallow channels for using a Laser Scanning Confocal Microscopy (LSCM, also referred to as CSLM, Confocal Scanning Laser Microscopy) for obtaining high resolution images and 3-D reconstructions of a variety of biological specimens.

Figure 10:
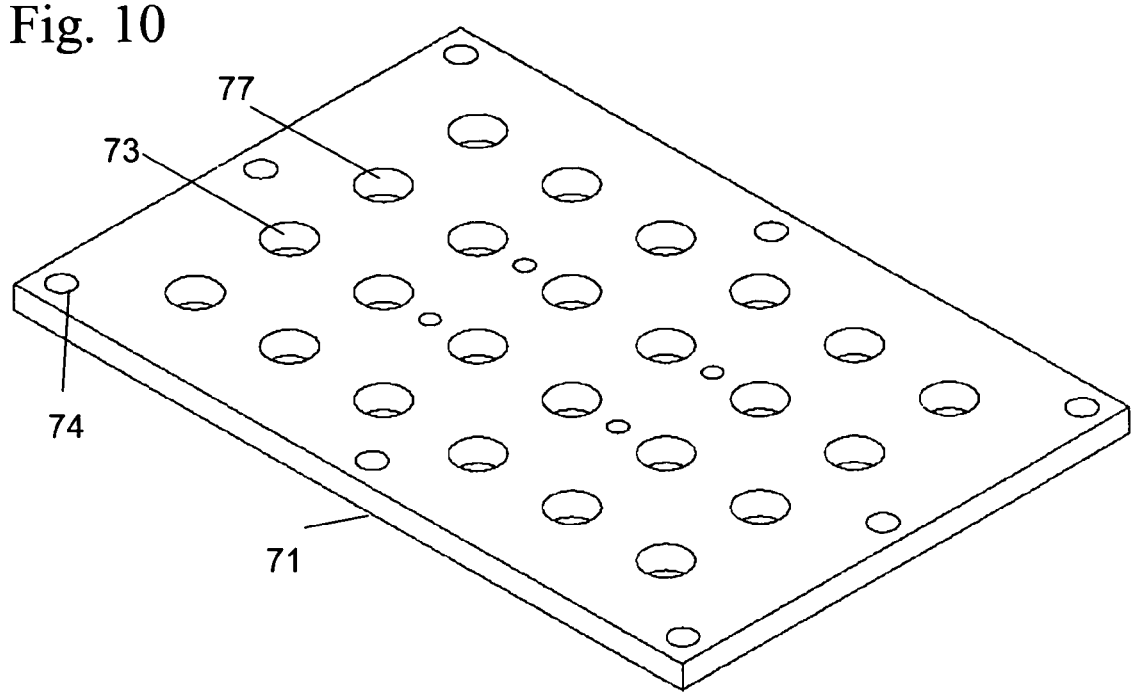
FIG. 10 shows an isometric view of the cover.

Once the chips are in place, the cover 71, shown in FIGS. 7 and 10 is then secured to the alignment base 70 by screws through holes 74 and 75. When the fluidic connectors or screws are tightened from the back of the alignment base in the threaded holes 93, the devices are forced together and seal to one another and the fluidic connections and the cover.

Figure 11:
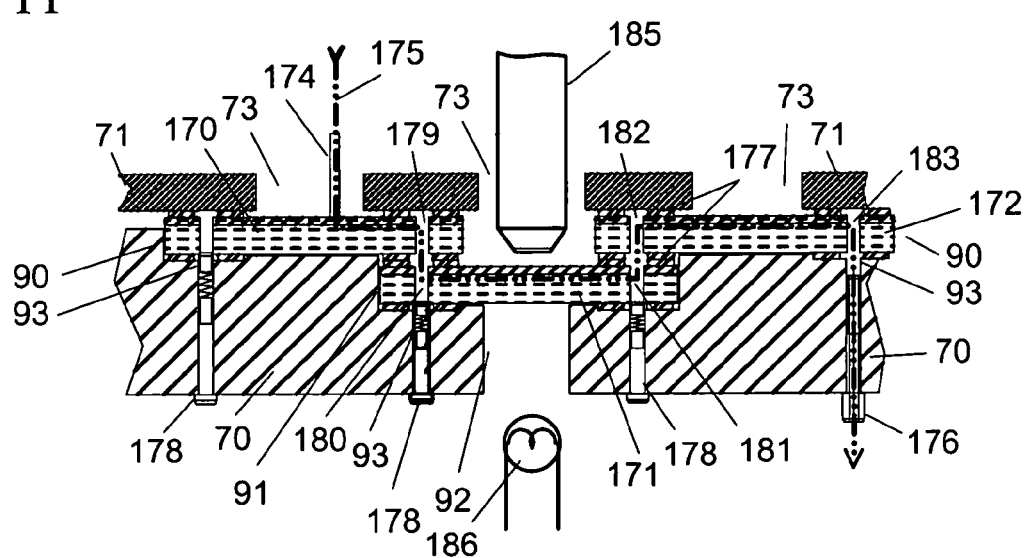
FIG. 11 shows a sectional detail of chip stacking, with the alignment base and cover.

FIG. 11 shows a detail of three chips 170, 171 and 172, assembled into the base 70 and with the cover 71 in place. As can be seen in the figure, chips 170 and 172 are in shallow wells 90, and chip 171 is in deep well 91.

Optical holes 92 allow access to the bottom of chip 171, and holes 73 allow access to the tops of chips 170 and 172, respectively. The objective of a microscope 185 is shown inspecting the fluid flow in chip 171 through the central cover hole 73. The chip is illuminated from underneath by light 186 directed through access hole 92 in the base.

Through-holes 93 can be seen in the base 70, with spring-loaded screws 178 in three of the holes. The spring-loaded screws apply a force to press the seals 177 of the chips against the cover 71, and also seal the bottom of the corner ports in the chip. The outlet port of chip 172 is routed through the back of the alignment base 70 using a threaded fitting 176. When the threaded fitting is tightened, it applies a force to seal the chip 172 against the cover, and also provides a route for fluid through the hollow center.

The fluid flowing through the example of FIG. 17 is shown as dashed line 175. It enters through a capillary fitting 174 in chip 170, then goes through a channel in the chip to corner port 179 and into corner port 180 in chip 171. The fluid then flows through chip 171 and out through corner port 181 into corner port 182 in chip 172. After flowing through chip 172, the flow leaves through corner port 183 into fitting 176 and out the bottom of the base 70.

Fabrication of the Invention

It is preferred that fluid devices described according to the present invention be fabricated using fabrication methods and equipment developed for the creation of microelectromechanical (MEMS) devices.

Dry etching of silicon, whether primarily physical in nature (ion-milling) or primarily chemical (plasma etching), is a highly evolved part of the overall fabrication process. Particularly preferred is Reactive-Ion Etching (RIE) or Deep Reactive Ion Etching (DRIE) techniques.

These techniques employ a combination of physical and chemical mechanisms, and are the most commonly practiced embodiment of dry etching. A particular class of silicon etch processes has been developed specifically for high-aspect-ratio etching of silicon in MEMS applications. See U.S. Pat. Nos. 4,784,720 and 4,855,017 (Lärmer et al.), for explicit descriptions of these specialized etch processes, collectively known as the "Bosch" process or Deep Reactive Ion Etching (DRIE).

The advantages of using DRIE process is its ability to produce very fine features, sizes on the order of 1 um. As the process is very anisotropic, meaning the etch is strongly preferential to a particular direction, the mask is very closely reproduced in the substrate. This is not the case for most RIE processes. Very often an RIE etch process will produce an undercut of the mask, limiting the control over fine feature sizes. Additionally, the lack of anisotropy in RIE etches limits the aspect ratio of the features being etched to near 1:1. With DRIE, one can obtain aspect ratios of 50:1, 1:50 or beyond.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A reconfigurable modular microfluidic system comprising:
   a) an alignment base comprising a plurality of wells;
   b) a plurality of microfluidic modules having a shape which corresponds to a shape of the wells and comprising a plurality of fluid communication ports located around a periphery of the microfluidic modules;

such that fitting the microfluidic modules into the wells of the alignment base forms a plurality of overlap regions for microfluidic modules in adjacent wells to align fluid communication ports in the overlap regions to form a plurality of direct fluid connections between the microfluidic modules; and c) a cover plate operatively connected to the alignment base, such that when the cover plate is mated with the alignment base, pressure is applied at each direct fluid connection of the microfluidic modules, such that a leak free module-to-module seal is formed at each direct fluid connection.

2. The system of claim 1, wherein fluidic access to at least one external device is possible at every fluid connection.

3. The system of claim 2, wherein the wells have a hole, which permits fluid communication to the fluid communication ports in the microfluidic modules through the alignment base.

4. The system of claim 3, wherein the holes are located in at least one corner of the wells.

5. The system of claim 2, wherein the cover plate has a plurality of holes, which permits fluid communication to the fluid communication ports in the microfluidic modules through the cover plate.

6. The system of claim 1, further comprising optical access to every microfluidic module, wherein the optical access allows for fluid visualization or molecular detection on each module.

7. The system of claim 6, wherein the cover plate comprises a plurality of apertures which provide optical access to the microfluidic modules.

8. The system of claim 6, wherein the alignment base further comprises a plurality of apertures which provide optical access to the microfluidic modules.

9. The system of claim 1, wherein the system is reconfigurable.

10. The system of claim 1, wherein the microfluidic modules further comprise an optically transparent lid, wherein the optically transparent lid is positioned to provide optical access to the microfluidic modules.

11. The system of claim 1, wherein the modules are selected from the group consisting of:
   a) functional modules, each performing a specific function;
   b) logic modules, directing a flow of fluid to a desired location;
   c) ingress/egress modules, providing a plurality of inlets and outlets for fluid in the system; and
   d) a combination of any of the above.

12. The system of claim 11, wherein the functional modules perform a biological or chemical function.

13. The system of claim 11, wherein the logic modules comprise an equal path length from fluid communication port to fluid communication port, such that the logic modules achieve a pressure balanced fluid flow.

14. The system of claim 11, further comprising at least one capillary tube which provides fluid to at least one ingress/egress module.

15. The system of claim 11, wherein the functional modules are selected from the group consisting of:
   a) a mixer;
   b) a liquid chromatagraphy column;
   c) a flow cell for use with a ultraviolet spectrometer;
   d) a liquid extraction column;
   e) a micropump;
   f) a heater;
   g) an electrospray apparatus;
   h) an electrophoresis apparatus;
   i) at least one reservoir;
   j) at least one reactor;
   k) at least one sensor; and
   l) any combination of a) through k).

16. The system of claim 1, wherein the microfluidic modules have a substantially square shape, such that the fluid communication ports are located at least at the corners of the microfluidic modules.

17. The system of claim 16, wherein the microfluidic modules are arranged in a diagonal array such that only one corner of adjacent microfluidic modules overlap.

18. The system of claim 1, further comprising a seal at each fluid communication port.

19. The system of claim 1, wherein each microfluidic module further comprises at least two layers.

20. The system of claim 19, wherein at least one of the layers is patterned with a pattern selected from the group consisting of:
   a) at least one fluid passageway;
   b) at least one feature of microfluidic architecture;
   c) at least one fluid communication port; and
   d) any combination of a), b), and c).

21. The system of claim 20, wherein the fluid communication ports are normal to a surface of the layers connecting to the microfluidic architecture.

22. The system of claim 19, wherein the layers are sealed together and form a microfluidic structure.

23. The system of claim 1, wherein the wells in the alignment base comprise a plurality of deep wells and a plurality of shallow wells.

24. The system of claim 23, wherein the plurality of deep wells alternates with the plurality of shallow wells.

25. The system of claim 24, wherein the fluid communication ports of the microfluidic modules located in the deep wells are aligned underneath the fluid communication ports of the microfluidic modules located in the shallow wells.

26. The system of claim 1, wherein at least one component of the system is fabricated by a method selected from the group consisting of:
   a) ion-milling;
   b) plasma etching;
   c) reactive-ion etching;
   d) deep reactive ion etching; and
   e) any combination of a) through d).

27. The system of claim 1, wherein the shape of the microfluidic modules comprises a consistent shape.

28. The system of claim 27, wherein the shape of the microfluidic modules is selected from the group consisting of:
   a) a square shape;
   b) a triangular shape;
   c) a rectangular shape;
   d) a hexagonal shape; and
   e) a circular shape.

29. The system of claim 27, wherein the shape of the microfluidic modules is a regular polygon.

30. The system of claim 1, wherein the fluid communication ports are located on at least one side of the microfluidic modules.

31. The system of claim 1, wherein at least one of the plurality of modules comprises at least one channel connecting at least two communication ports of the at least one module.

* * * * *